(12) United States Patent
Zink et al.

(10) Patent No.: US 10,888,643 B2
(45) Date of Patent: Jan. 12, 2021

(54) NEGATIVE PRESSURE INTERBODY DEVICE, SYSTEM, AND METHOD

(71) Applicants: Thomas Zink, San Antonio, TX (US); Zeshan Hyder, Munster, IN (US); Frank Kuwamura, III, San Antonio, TX (US); Nicholas Cordaro, Vista, CA (US)

(72) Inventors: Thomas Zink, San Antonio, TX (US); Zeshan Hyder, Munster, IN (US); Frank Kuwamura, III, San Antonio, TX (US); Nicholas Cordaro, Vista, CA (US)

(*) Notice: Subject to any disclaimer, the term of this patent is extended or adjusted under 35 U.S.C. 154(b) by 35 days.

(21) Appl. No.: 16/146,301

(22) Filed: Sep. 28, 2018

(65) Prior Publication Data

US 2019/0105432 A1 Apr. 11, 2019

Related U.S. Application Data

(60) Provisional application No. 62/569,526, filed on Oct. 7, 2017.

(51) Int. Cl.
*A61F 2/44* (2006.01)
*A61M 1/00* (2006.01)
(Continued)

(52) U.S. Cl.
CPC .............. *A61M 1/008* (2013.01); *A61F 2/447* (2013.01); *A61F 2/4465* (2013.01);
(Continued)

(58) Field of Classification Search
CPC .... A61M 1/008; A61M 1/0088; A61M 1/005; A61M 1/0023; A61M 1/0037; A61M 1/0056; A61M 2205/04; A61M 2205/3379; A61M 2205/7518; A61M 2205/7545; A61M 16/06; A61M 27/00; A61M 2210/02; A61M 2210/1003; A61F 2/4465; A61F 2/447; A61F 2/442; A61F 2/4455; A61F 13/00068; A61F 13/0226; A61F 13/0246; A61F 2002/30593; A61F 2002/30622;
(Continued)

(56) References Cited

U.S. PATENT DOCUMENTS

| | | | |
|---|---|---|---|
| 6,358,197 B1 * | 3/2002 | Silverman | A61F 2/04 600/29 |
| 8,216,316 B2 * | 7/2012 | Kirschman | A61F 2/447 606/99 |

(Continued)

*Primary Examiner* — Pedro Philogene
(74) *Attorney, Agent, or Firm* — Brennan, Manna & Diamond, LLC

(57) ABSTRACT

An implantable interbody negative pressure device that permits reduced or negative pressure therapies to be applied to a portion of a patient's body. More specifically, the implantable interbody negative pressure device comprises a body portion having a plurality of openings in fluid communication with both an internal passageway and a vacuum source, and that serves as a manifold and permits reduced or negative pressure therapy to be applied to a surgical site, such as a wound or damaged bone. The application of the reduced or negative pressure to the body improves circulation and the disposal of cellular waste, and promotes bone growth and healing.

20 Claims, 4 Drawing Sheets

(51) Int. Cl.
    *A61F 13/00* (2006.01)
    *A61F 2/30* (2006.01)
(52) U.S. Cl.
    CPC ..... *A61F 13/00068* (2013.01); *A61M 1/0088* (2013.01); *A61F 2002/30593* (2013.01); *A61F 2002/30622* (2013.01); *A61F 2002/30828* (2013.01); *A61M 2205/04* (2013.01); *A61M 2210/02* (2013.01); *A61M 2210/1003* (2013.01)
(58) Field of Classification Search
    CPC .. A61F 2002/30828; A61F 2002/30112; A61F 2002/3093; A61F 2002/30387; A61F 2002/30784; A61F 2002/30787; A61F 2002/3082; A61F 2002/30677; A61F 2002/302; A61F 2013/00919; A61B 90/00; A61B 2017/00557; A61B 2017/306
    USPC .......... 623/17.11–17.16; 602/42–53; 128/897–898
    See application file for complete search history.

(56) References Cited

U.S. PATENT DOCUMENTS

| | | | |
|---|---|---|---|
| 9,549,822 B2* | 1/2017 | Wimberley | A61F 2/4455 |
| 10,625,066 B2* | 4/2020 | Kantrowitz | A61M 1/28 |
| 2010/0036367 A1* | 2/2010 | Krohn | A61M 1/0088 604/543 |
| 2010/0262126 A1* | 10/2010 | Hu | A61M 1/0088 604/543 |
| 2014/0052258 A1* | 2/2014 | Ball | A61F 2/442 623/17.16 |
| 2018/0221173 A1* | 8/2018 | Moskowitz | A61F 2/447 |

* cited by examiner

NEGATIVE PRESSURE INTERBODY DEVICE, SYSTEM, AND METHOD

CROSS-REFERENCE TO RELATED APPLICATION

This application claims priority from Provisional Patent Application Ser. No. 62/569,526 filed on Oct. 7, 2017, which is incorporated herein by reference.

FIELD OF THE INVENTION

The present invention relates generally to an implantable device positioned near bone and, in particular, to an interbody device that acts like a manifold when negative pressure is applied to the surgical site. The present subject matter is especially suitable for interbody PEEK devices, such as anterior lumbar interbody fusion (ALIF) devices and posterior lumbar interbody fusion (PLIF) devices. Accordingly, the present specification makes specific reference thereto. However, it is to be appreciated that aspects of the present inventive subject matter are also equally amenable to other similar applications.

BACKGROUND

Reduced pressure and negative pressure therapy devices are known in the art for assisting with the healing of an open wound. Such devices typically comprise both a sealant layer and a suction apparatus. The sealant layer is used to create a sealed enclosure between the device and the surface of a patient by forming, preferably, an airtight seal around an area of wounded tissue that requires negative or reduced pressure therapy. The suction apparatus is typically in communication with the sealant layer, and functions so as to reduce the amount of pressure present underneath the sealant layer. Together, the combination of the sealant layer and the suction apparatus create a closed reduced pressure therapy system. By introducing reduced pressure to a wound, circulation is improved and cellular waste is removed, both of which promote healing.

Additionally, it has been determined that applying negative pressure to bone that has been subjected to a traumatic event promotes bone healing, as well as bone growth. Current methods of applying negative or reduced pressure to an affected bone, such as a vertebra, involve placing a manifold with a tube in communication therewith in the surgical site and then closing the patient with the opposite end of the tube extending outside of the patient's body. The portion of the tube that extends outside the patient's body may then be connected to a pump that is used to remove or reduce pressure from the surgical site to start a cascade of healing on the affected bone. The cascade accelerates the healing of the bone, promotes bone growth, and, when performed on the spine, the fusion of vertebra.

However, said prior art negative or reduced pressure therapies are not without their limitations. For example, post-operatively, the manifold can become dislodged from the surgical site, for example, due to movement of the patient. If this happens, not only is the manifold dislodged within the patient, but negative pressure can no longer be applied to the bone and the benefits of applying negative pressure to increase bone healing and promote bone growth are lost.

Additionally, it is difficult to determine if the manifold has become dislodged from the surgical site unless the patient is x-rayed or re-opened, neither of which is ideal for a post-operative patient. For example, additional x-rays to locate the manifold expose the patient to unnecessary radiation, which is both undesirable and potentially dangerous. Also, additional surgery exposes the patient to undesirable risks such as those associated with anesthesia, the risk of infection, not to mention pain, discomfort, missed work and the expense of the additional surgical procedure to remove or reattach the manifold.

Consequently, there exists a long felt need in the art for a negative pressure device and/or system that permits reduced or negative pressure therapies to be applied to a surgical site without the risk of subsequent disconnection or loss of negative pressure. There also exists a long felt need in the art for an interbody negative pressure device and/or system that permits reduced or negative pressure therapies to be applied to a surgical wherein it is not necessary for the patient to undergo a second invasive procedure at the conclusion of the therapy. Additionally, there is a long felt need for an interbody negative pressure device and/or system that overcomes the limitations of the prior art, and that is safe and easy to use.

The present invention discloses an implantable interbody negative pressure device comprising a plurality of openings therein which serves as a manifold and permits reduced or negative pressure therapy to be applied to a surgical site, such as a wound or damaged bone. A tube may be releasably attached to the interbody device so that reduced or negative pressure can be applied. The application of the reduced or negative pressure to the surgical site improves circulation and the disposal of cellular waste. Further, reduced or negative-pressure therapy applied to a bone accelerates the healing of the bone, promotes bone growth, and, when performed on the spine, the fusion of the vertebra.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

Generally stated, reduced or negative-pressure wound therapy is a therapeutic technique using a vacuum dressing to promote healing in acute or chronic wounds and to enhance healing. Reduced or negative-pressure therapy are also useful for treating bone that has been traumatized and to accelerate the healing of the bone, promote bone growth, and, when performed on the spine, the fusion of the vertebra.

In accordance with an aspect of the invention, a device and a method are disclosed which provides reduced and/or negative-pressure to the surgical site, such as bone, to promote bone healing and growth. In one embodiment of the present invention, the implantable device of the present comprises an interbody cage comprised of a plurality of holes or openings which serves as a manifold that can be used to apply reduced or negative-pressure to the surgical site. Specifically, the interbody cage device comprises a plurality of openings leading to an interior passageway of the device, whereby reduced or negative pressure is permitted to pass through the openings and onto the affected bone or other wound. Further, a tube is releasably attached to or in communication with both the interbody device and a pump so that the reduced or negative pressure can be applied to the area to be treated with the therapy. Because the tube is releasably attached to the interbody cage, it can be removed from the patient at the conclusion of the negative pressure therapy without the need for a second invasive procedure. Reducing the number of invasive procedures that a patient is subjected to, also reduces all of the risks and other drawbacks typically associated therewith including, without limitation, the risks associated with anesthesia, infection, pain, discomfort, missed work and the expense and inconvenience of the secondary procedure.

In another embodiment of the present invention, a method of applying reduced or negative pressure to a wound or affected bone is disclosed and comprises the steps of: (a) applying an interbody cage with a plurality of openings therein to an affected bone; (b) releasably attaching a length of tube to both the interbody cage and a suction device, such as a pump; and (c) using said suction device to pull pressure from the interbody cage through one or more of said plurality of openings and said tube. The method of the present invention reduces pressure adjacent to the affected bone and/or wound, thereby, increasing circulation, disposing of cellular waste, accelerating the healing of the bone, promoting bone growth, and, when performed on the spine, the fusion of the vertebra.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

While the specification concludes with claims particularly pointing out and distinctly claiming the present invention, it is believed that the present invention will be better understood from the following description in conjunction with the accompanying FIGS., in which like reference numerals identify like elements, and wherein:

DETAILED DESCRIPTION

Figure 1:
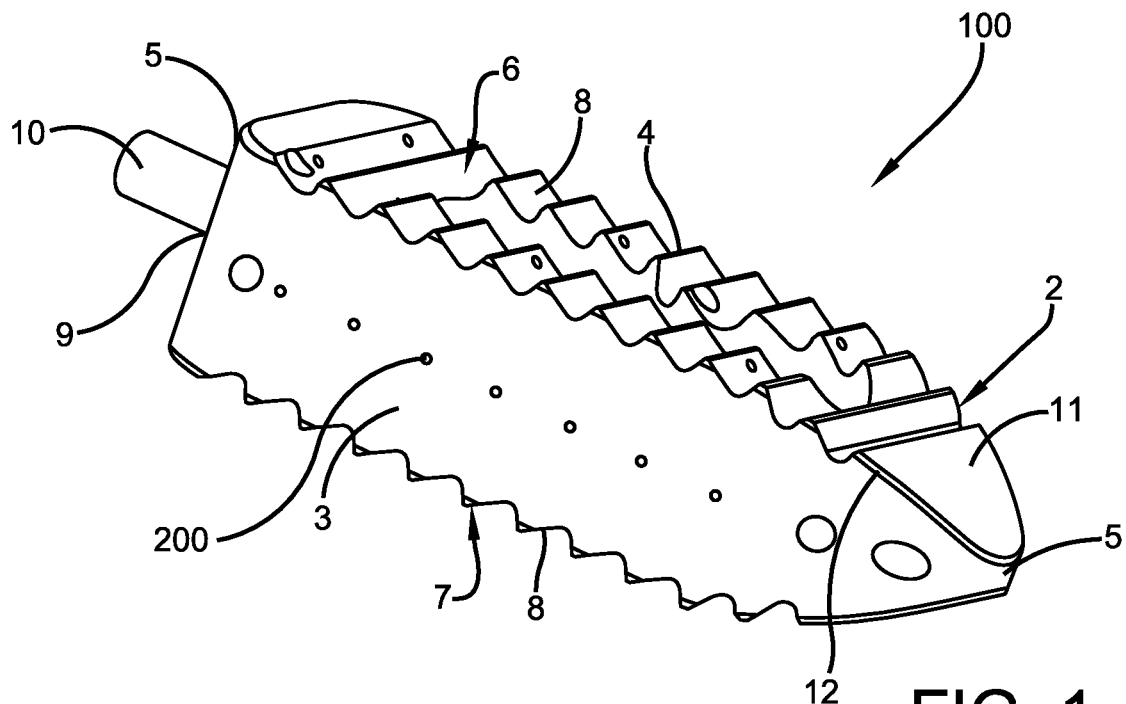
FIG. 1 illustrates a side perspective view of a posterior lumbar interbody fusion (PLIF) device with a plurality of openings therein and releasably attached to a length of tubing, all in accordance with the disclosed architecture.

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Further, the reduced or negative-pressure device and method of the present invention is especially suitable for interbody PEEK devices, such as ALIF devices and PLIF devices. Accordingly, the present specification makes specific reference thereto. However, it is to be appreciated that aspects of the present inventive subject matter are also equally amenable to other similar devices and applications and, therefore, should not be construed as limitations.

By way of background, and generally stated, a PLIF procedure typically involves adding material such as bone graft to an area of the spine to provoke a biological response that causes the bone to grow between the two vertebral elements. In such a procedure, the surgeon typically approaches the spine through a three-inch to six-inch long incision in the midline of the back and the left and right lower back muscles are removed from the lamina on both sides, and at multiple levels. Next, the lamina is removed (i.e., laminectomy) which allows visualization of the nerve roots. The facet joints, which are directly over the nerve roots may then be trimmed to give the nerve roots more room. The nerve roots are then retracted to one side, and the disc space is cleaned of the disc material. Following the cleaning of the disc space, a cage made of allograft bone, or posterior lumbar interbody cage with bone graft, is then inserted into the disc space and the bone grows from vertebral body to vertebral body.

An ALIF procedure is similar to the PLIF procedure, except that in the ALIF procedure, the disc space is fused by approaching the spine through the abdomen instead of through the lower or middle back. More specifically, in the ALIF approach, a three-inch to five-inch incision is made on the left side of the abdomen to approach the spine, and an ALIF cage made of allograft bone, or an anterior lumbar interbody cage with bone graft, is then inserted into the disc space and the bone grows from vertebral body to vertebral body.

The present invention discloses an implantable, interbody device, such as a PLIF or ALIF device, that comes in contact with bone, such as vertebra, and a related method of applying reduced or negative-pressure therapy to said bone. In one embodiment of the present invention, the implantable device of the present comprises an interbody cage comprised of a plurality of holes or openings which serves as a manifold that can be used to apply reduced or negative-pressure to the surgical site. Specifically, the interbody cage device comprises a plurality of openings leading to an interior passageway of the device, whereby reduced or negative pressure is permitted to pass through the openings and onto the affected bone or other wound. Further, a tube is releasably attached to or in communication with both the interbody device and a pump so that the reduced or negative pressure can be applied to the area to be treated with the negative pressure therapy. Because the tube is releasably attached to the interbody cage, it can be removed from the patient at the conclusion of the negative pressure therapy without the need for a second invasive procedure.

Referring initially to the drawings, FIG. 1 illustrates a side perspective view of an implantable PLIF interbody cage device 100 of the present invention releasably attached to a length of tubing 10, all in accordance with the disclosed architecture. More specifically, the interbody cage device 100 comprises a body portion 2 with a substantially parallel posterior 3 and anterior 4 sidewalls separated by two narrow implant ends 5, superior 6 and inferior 7 faces each having a plurality of undulating surfaces 8 for contacting adjacent upper and lower vertebral endplates (not shown). Undulating surfaces 8 are preferably comprised of a plurality of alternating ridges and valleys that help device 100 grip the adjacent structure (be it vertebra or additional implants) and reduce the likelihood of device 100 repositioning itself once properly installed.

Figure 2:
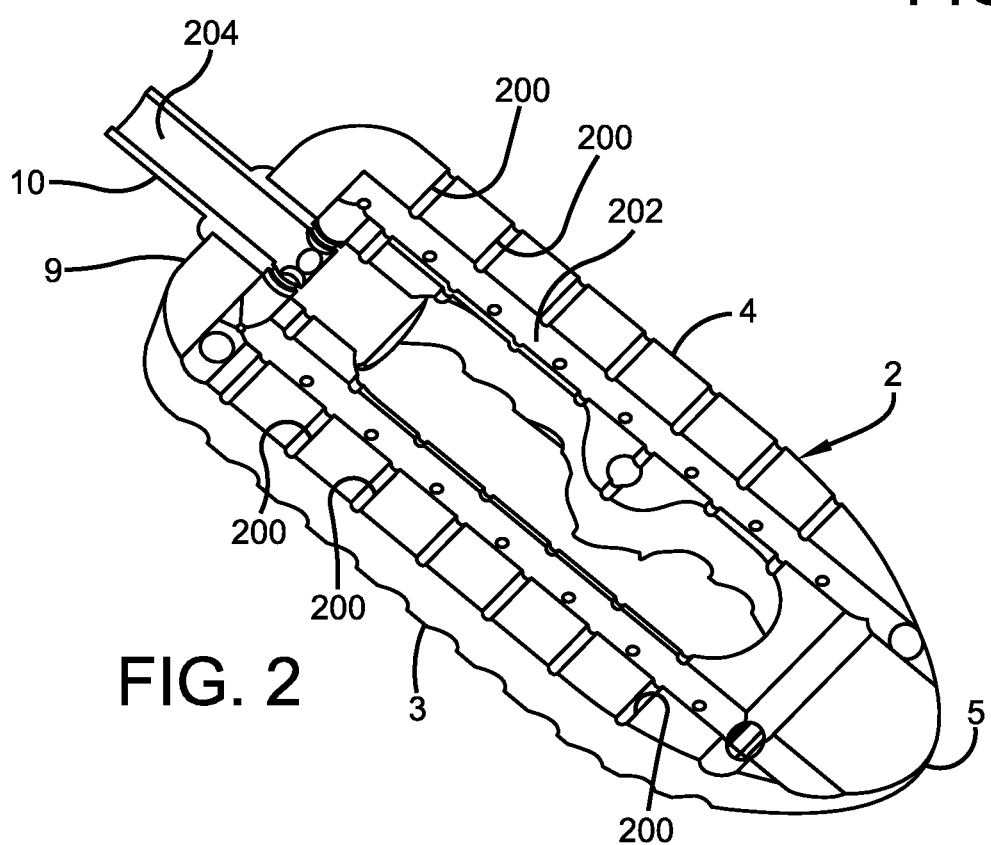
FIG. 2 illustrates a cross-sectional view of the PLIF device and associated tubing of FIG. 1 illustrating the interior passageways, all in accordance with the disclosed architecture.

As best shown in FIGS. 1 and 2, interbody cage device 100 and body portion 2 further comprise at least one depression 9 in the implant end 5 adjacent to tube 10 for engagement by an insertion tool (not shown), a chamfer 11 on the superior 6 and inferior 7 faces of at least one of the narrow implant ends 5, and a rounded edge 12 along a perimeter of the superior 6 and inferior 7 faces. The chamfers 11 on the superior 6 and inferior 7 faces at the narrow end 5 facilitate insertion of the implant device 100 in an oblique or standard posterior approach so that a single cage device 100 provides balanced support to the spinal column.

As stated above, the interbody cage device 100 can be any suitable size, shape, and/or configuration as is known in the art without affecting the overall concept of the invention. One of ordinary skill in the art will appreciate that the shape, size and configuration of the interbody cage device 100, as shown in FIGS. 1 and 2, is for illustrative purposes only, and that many other shapes and sizes of the interbody cage device 100 are well within the scope of the present disclosure. Although the dimensions of the interbody cage device 100 (i.e., length, width, and height) are important design parameters for good performance, the interbody cage device 100 may be any shape or size that ensures optimal performance during use and/or that suits user preference.

Additionally, the interbody cage device 100 comprises a plurality of holes or openings 200 preferably positioned in spaced apart fashion around the posterior and anterior sidewalls 3 and 4, and that are interconnected and in fluid communication with an internal passageway 202, as best shown in the cross-sectional view of PLIF device 100 depicted in FIG. 2. Notwithstanding; openings 200 are not specifically limited to the posterior and anterior sidewalls 3 and 4, and may also be positioned elsewhere along body portion 2 such as on undulating surfaces 8, narrow implant ends 5, superior and inferior faces 6, 7, etc., without affecting the overall concept of the present invention.

More specifically, the openings 200 preferably extend from an outer surface of device 100 to passageway 202, which is interior to the interbody cage device 100. Passageway 202 connects with the plurality of openings 200 to permit air to circulate throughout the interbody cage device 100, and also circulate near the adjacent bone to accelerate healing and promote bone growth.

As referenced above, PLIF interbody cage device 100 is preferably releasably attached to length of tubing 10 which is, in turn, preferably attached to a pump or other vacuum source (not shown). More specifically, tubing 10 has a continuous opening 204 therein and is releasably attached to an end 5 of the interbody cage device 100 such that opening 204 is in fluid communication with the plurality of openings and internal passageway 202. In this manner, the pump or other vacuum attached to the opposite end of tubing 10 can apply negative pressure to device 100 and the immediate surrounding area and/or bone by pulling or vacuuming air through the plurality of openings 200, passageway 202 and tubing 10, thereby creating a cascade of healing on the affected bone and fusion of the vertebra in close proximity to device 100. Further, because tubing 10 is releasably attached to device 100, it can easily be detached from the device and removed from the patient (not shown) without the need for a second invasive procedure and all of the risks associated therewith.

Typically, the interbody PLIF cage device 100 of the present invention may be manufactured using additive manufacturing (AM) techniques, or using a combination of other molding or machining techniques (e.g., injection molding, machining, etc.) to produce the device 100. These additional techniques include, without limitation, material extrusion, vat photo polymerization, powder bed fusion, material jetting, binder jetting, sheet lamination and directed energy deposition. Typically, the interbody PLIF cage device 100 is manufactured from PEEK, titanium, specifically Ti 6 Al 4 V-ELI, but can be manufactured from any other suitable material as is known in the art for use in an implant.

Figure 3:
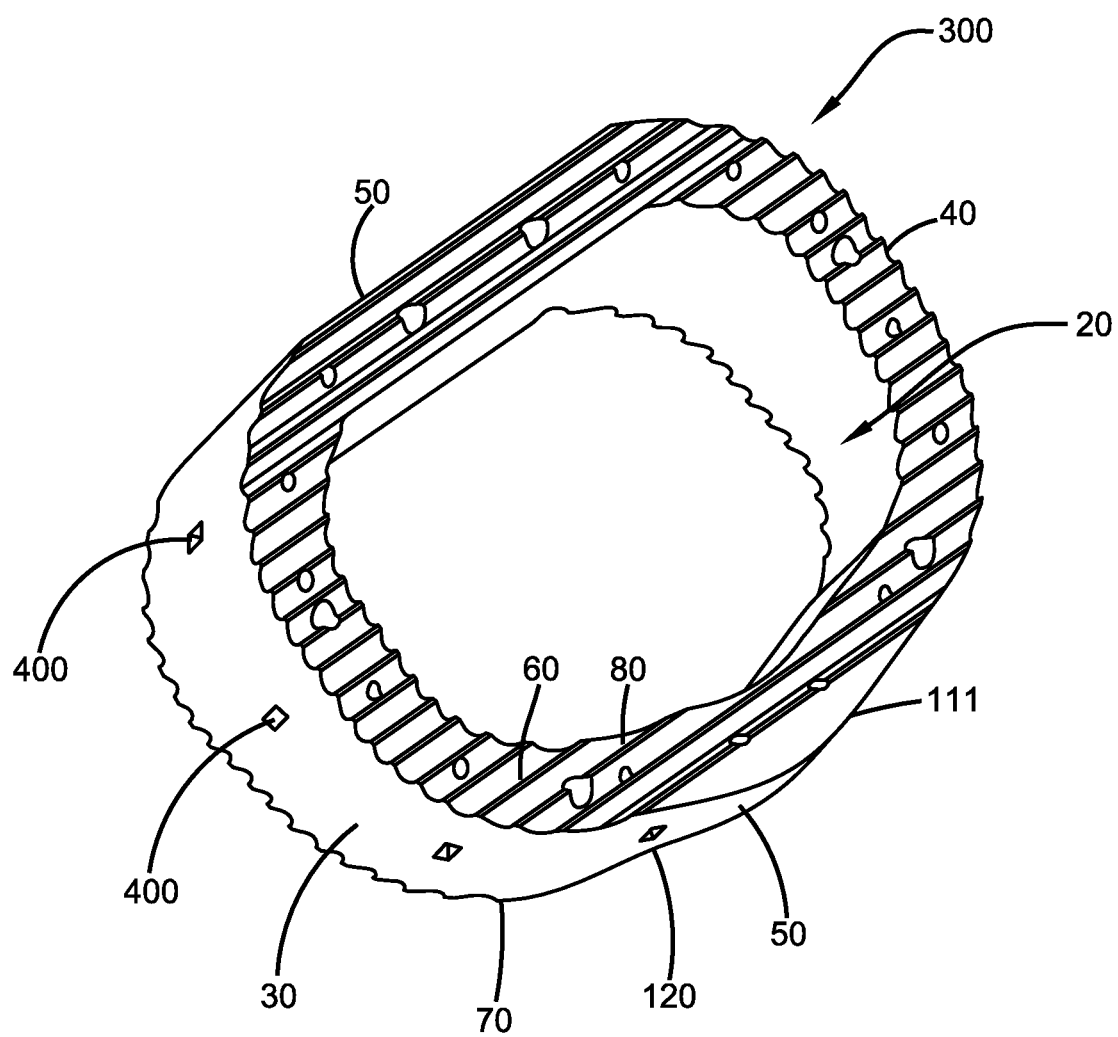
FIG. 3 illustrates a top perspective view of an anterior lumbar interbody fusion (ALIF) device with a plurality of openings therein, all in accordance with the disclosed architecture.
Figure 4:
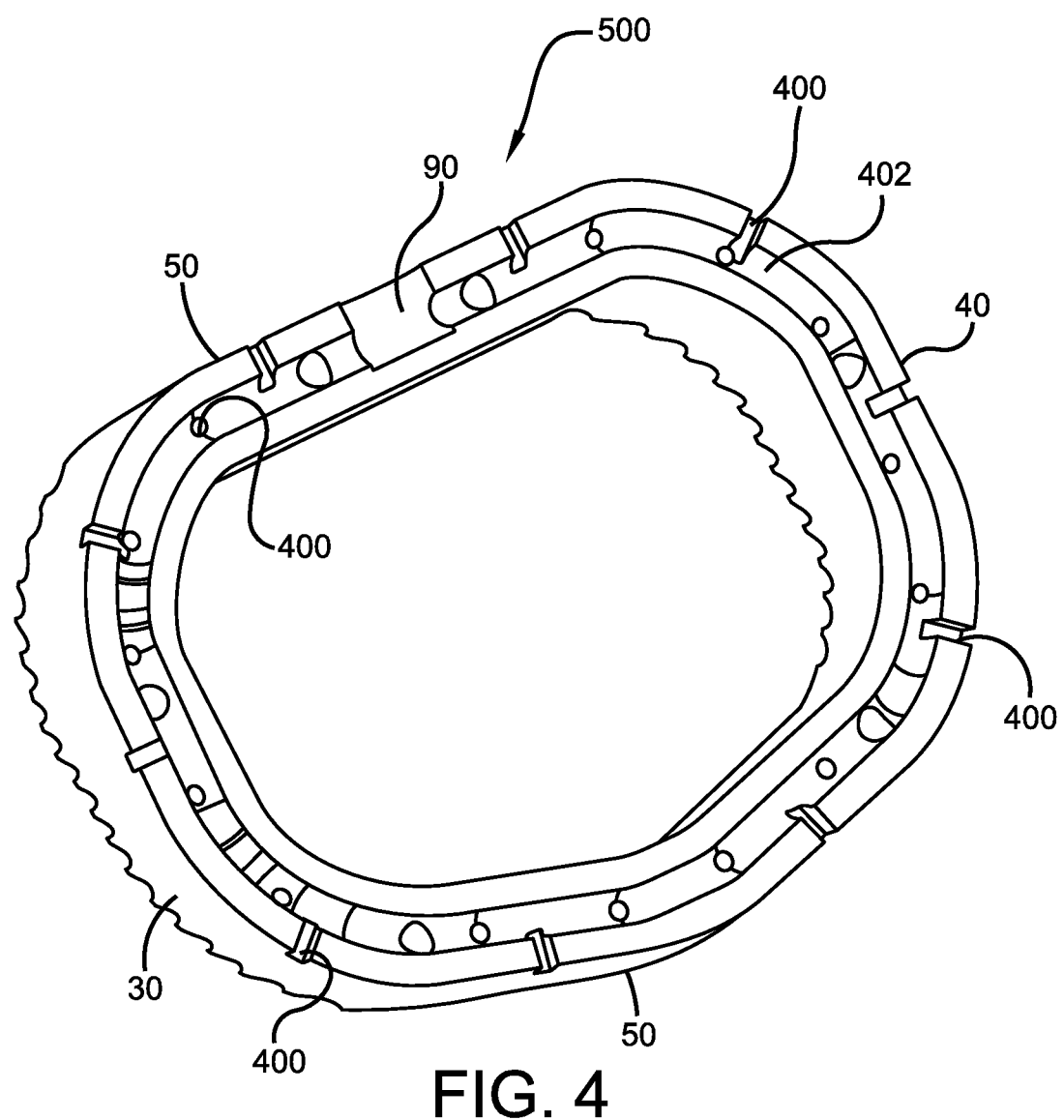
FIG. 4 illustrates a cross-sectional view of the ALIF device of FIG. 3 illustrating the interior passageways and releasably attached to a length of tubing, all in accordance with the disclosed architecture.
Figure 5:
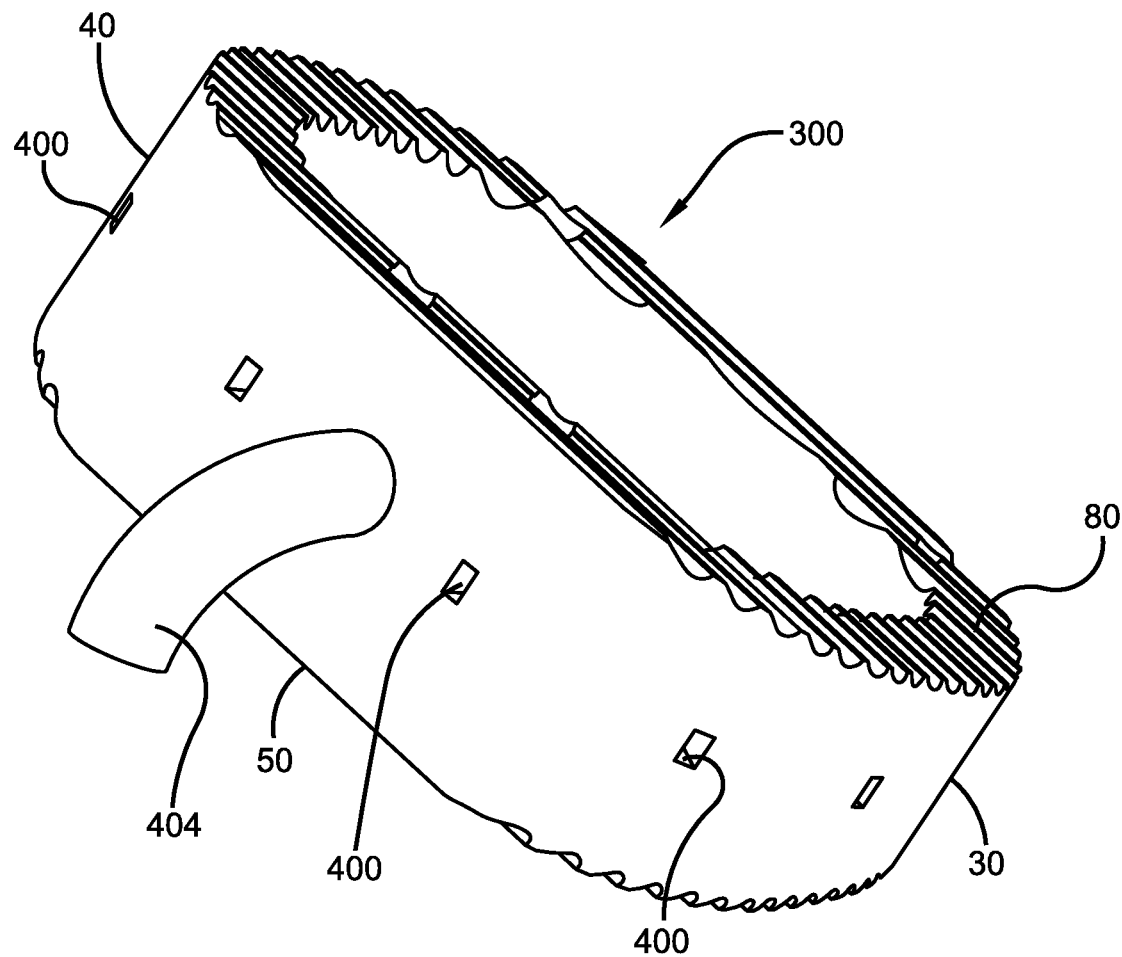
FIG. 5 illustrates a side perspective view of the interbody ALIF device of FIG. 3 releasably attached to a length of tubing, all in accordance with the disclosed architecture.

FIGS. 3-5 illustrate yet another potential embodiment of the implantable negative interbody device of the present invention, specifically an ALIF device 300. The interbody ALIF cage device 300 preferably comprises a body portion 20 with substantially parallel posterior 30 and anterior 40 sidewalls separated by two implant ends 50, superior 60 and inferior 70 faces having a plurality of undulating surfaces 80 for contacting upper and lower vertebral endplates (not shown). As described above, the undulating surfaces 80 are preferably comprised of a plurality of alternating ridges and valleys that help device 300 grip the adjacent structure (be it vertebra or additional implants) and reduce the likelihood of device 100 repositioning itself once properly installed.

As best shown in FIG. 4, interbody cage device 300 and body portion 20 further comprise at least one depression 90 in implant end 50 for engagement by an insertion tool (not shown), a chamfer 111 on the superior 60 and inferior 70 faces of at least one of the implant ends 50, and a rounded edge 120 along a perimeter of the superior 60 and inferior 70 faces. The chamfers 111 on the superior 60 and inferior 70 faces at the end 50 facilitate insertion of the implant device 300 in a standard anterior approach so that a single cage device 300 provides balanced support to the spinal column.

As stated above, the interbody cage device 300 can be any suitable size, shape, and/or configuration as is known in the art without affecting the overall concept of the invention. One of ordinary skill in the art will appreciate that the shape, size and/or configuration of the interbody cage device 300, as shown in FIGS. 3-5, is for illustrative purposes only, and that many other shapes and sizes of the interbody cage device 100 are well within the scope of the present disclosure. Although the dimensions of the interbody cage device 300 (i.e., length, width, and height) are important design parameters for good performance, the interbody cage device 300 may be any shape or size that ensures optimal performance during use and/or that suits user preference.

Additionally, the interbody cage device 300 comprises a plurality of holes or openings 400 preferably positioned in spaced apart fashion around the posterior and anterior sidewalls 30, 40, and that are interconnected and in fluid communication with an internal passageway 402, as best shown in the cross-sectional view of ALIF device 300 depicted in FIG. 4. Notwithstanding, openings 400 are not specifically limited to the posterior and anterior sidewalls 30 and 40, and may also be positioned elsewhere along body portion 20 such as on undulating surfaces 80, implant ends 50, superior and inferior faces 60, 70, etc., without affecting the overall concept of the present invention.

More specifically, the openings 400 preferably extend from an outer surface of ALIF device 300 to passageway 402, which is interior to the interbody device 300. Passageway 402 connects with the plurality of openings 400 to permit air to circulate throughout the interbody cage device 300, and also circulate near the adjacent bone to accelerate healing and promote bone growth.

As referenced above, ALIF interbody cage device 300 is preferably releasably attached to length of tubing 404 which is, in turn, preferably attached to a pump or other vacuum source (not shown). More specifically, tubing 404 has a continuous opening therein (not shown) and is releasably attached to an end 50 of the interbody cage device 300 such that tubing 404 is in fluid communication with the plurality of openings 400 and internal passageway 402. In this manner, the pump or other vacuum attached to the opposite end of tubing 404 can apply negative pressure to device 300 and the immediate surrounding area and/or bone by pulling or vacuuming air through the plurality of openings 400, passageway 402 and tubing 404, thereby creating a cascade of healing on the affected bone and fusion of the vertebra in close proximity to device 300. Further, because tubing 404 is releasably attached to ALIF device 300, it can easily be detached from the device and removed from the patient (not shown) without the need for a second invasive procedure and all of the risks associated therewith.

Typically, the interbody cage device 300 of the present invention may be manufactured using additive manufacturing (AM) techniques, or using a combination of other molding or machining techniques (e.g., injection molding, machining, etc.) to produce the device. These additional techniques include, without limitation, material extrusion, vat photo polymerization, powder bed fusion, material jetting, binder jetting, sheet lamination and directed energy deposition. Typically, the interbody cage device 300 is manufactured from PEEK, titanium, specifically Ti 6 Al 4 V-ELI, but can be manufactured from any other suitable material as is known in the art for use in a sterile implant.

In a further embodiment, the interbody cage device 300 can be manufactured as two separate halves 500 (one of half of which is shown in FIG. 4) and then screwed together (or attached to one another by any other means commonly known in the art) to form the interbody cage device 300. The halves 500 may be formed to allow for manufacturing of the passageway 402. Specifically, the passageway 402 would be machined in to each half 500 and then the halves 500 are secured together to form the complete passageway 402.

Having described generally a few of the various embodiments of the negative pressure interbody device of the present invention, a method of applying reduced or negative-pressure to a wound or affected bone, such as vertebra, will now be discussed. More specifically, in one embodiment of the present invention, and by way of example, the method of applying reduced or negative-pressure to an affected bone is comprised of the steps of: (a) applying an interbody cage device with a plurality of openings therein to a affected bone or wound; (b) releasably attaching a first end of a length tube to both the interbody cage and a vacuum or suction device, such as a pump; and (c) using said vacuum device to pull pressure from the interbody cage (and its immediately surrounding areas) through one or more of said plurality of openings and said tube. The method of the present invention reduces pressure adjacent to the affected bone and/or wound, thereby, increasing circulation, disposing of cellular waste, accelerating the healing of the bone, promoting bone growth, and, when performed on the spine, the fusion of the vertebra.

The interbody cage device referenced in the above method can be either of the devices described supra, namely a PLIF or ALIF cage, some variation thereof, or any other suitable implant device that comprises the above described structure, namely a body portion with a plurality or openings formed therein in fluid communication with an internal passageway and a vacuum source.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable device for providing negative pressure therapy to an internal area of the body comprising:
    a body portion, wherein said body portion further comprises a posterior sidewall and an anterior sidewall;
    an internal passageway; and
    a plurality of openings in an outermost exterior surface of the anterior and posterior sidewalls, wherein said plurality of openings is in fluid communication with the internal passageway and a vacuum source.

2. The implantable device of claim 1, wherein said body portion further comprises at least one undulating surface.

3. The implantable device of claim 1, wherein said internal passageway is in fluid communication with the vacuum source.

4. The implantable device of claim 1 further comprising a length of tube extending out of the body and in fluid communication with both the internal passageway and the plurality of openings.

5. The implantable device of claim 1 further comprising at least one depression for engagement with an insertion tool.

6. The implantable device of claim 1, wherein said body portion further comprises a superior face and an inferior face.

7. The implantable device of claim 6, wherein at least one of said superior and inferior faces further comprise a chamfered surface.

8. The implantable device of claim 1, wherein the body portion is comprised of at least two sections fixedly attached to one another.

9. A system for providing negative pressure therapy to an internal area of the body comprising:
    an implantable device comprised of a body portion comprised of a posterior sidewall and an anterior sidewall, a plurality of openings in an outermost exterior of the posterior sidewall and the anterior sidewall, and an internal passageway;
    a length of tubing having a first end extending outside of the body and a second end positioned within the body; and
    a vacuum source.

10. The system of claim 9, wherein said body portion further comprises a superior face and an inferior face.

11. The system of claim 10, wherein at least one of said superior and inferior faces further comprise a chamfered surface.

12. The system of claim 9, wherein said implantable device is in fluid communication with the length of tubing and the length of tubing is in fluid communication with the vacuum source.

13. The system of claim 9, wherein the implantable device is further comprised of at least one undulating surface.

14. The system of claim 9, wherein the implantable device is an anterior lumbar interbody fusion device.

15. The system of claim 9, wherein the implantable device is a posterior lumbar interbody fusion device.

16. The system of claim 9, wherein the implantable device is comprised of titanium and at least two sections fixedly attached to one another.

17. A method of providing negative pressure therapy to an area of the body comprising the steps of:
   (a) applying an interbody cage device to the area, wherein the interbody cage device is comprised of a posterior sidewall, an anterior sidewall, an internal passageway, and a plurality of openings in an outermost exterior of the anterior and posterior sidewalls, and further wherein the plurality of openings are in fluid communication with the internal passageway;
   (b) releasably attaching a first end of a length tube to the interbody cage device inside of the body;
   (c) attaching a second end of the length of tube to a vacuum source positioned outside of the body; and
   (d) using the vacuum source to create a negative pressure environment in and around the interbody cage device, wherein the vacuum source is in fluid communication with the plurality of openings.

18. The method of claim 17, wherein the interbody cage device is comprised of a body portion.

19. The method of claim 18, wherein wherein said body portion is further comprised of a superior face and an inferior face, wherein each of the superior and inferior faces further comprise a chamfered surface.

20. The method of claim 18, wherein the body portion is further comprised of at least one undulated surface.

\* \* \* \* \*